(12) United States Patent
Masuch

(10) Patent No.: US 7,479,197 B2
(45) Date of Patent: Jan. 20, 2009

(54) THIN-LAYER CELL

(75) Inventor: Ralf Masuch, Freiburg (DE)

(73) Assignee: micro-biolytics GmbH, Freiburg (DE)

( * ) Notice: Subject to any disclaimer, the term of this patent is extended or adjusted under 35 U.S.C. 154(b) by 372 days.

(21) Appl. No.: 10/530,956

(22) PCT Filed: Oct. 8, 2003

(86) PCT No.: PCT/EP03/11126

§ 371 (c)(1),
(2), (4) Date: Feb. 23, 2006

(87) PCT Pub. No.: WO2004/036193

PCT Pub. Date: Apr. 29, 2004

(65) Prior Publication Data

US 2006/0175732 A1    Aug. 10, 2006

(30) Foreign Application Priority Data

Oct. 9, 2002    (DE) ............................... 102 47 020

(51) Int. Cl.
*C03C 27/00* (2006.01)
*G01N 21/00* (2006.01)
*G01N 21/49* (2006.01)
*G01N 21/85* (2006.01)

(52) U.S. Cl. .................. 156/99; 156/106; 156/107; 250/576; 356/246; 356/440; 422/58; 422/68.1; 422/82.09

(58) Field of Classification Search ................ 156/99, 156/105, 106, 107; 250/576; 356/246, 410, 356/440; 378/47, 79; 422/58, 68.1, 82.05, 422/82.09, 100, 101, 102, 103, 104
See application file for complete search history.

(56) References Cited

U.S. PATENT DOCUMENTS

| 4,911,782 A | 3/1990 | Brown |
| 6,117,395 A | 9/2000 | Ploug et al. |

(Continued)

FOREIGN PATENT DOCUMENTS

DE    41 37 060    5/1993

(Continued)

*Primary Examiner*—Jeff Aftergut
*Assistant Examiner*—Brian R Slawski
(74) *Attorney, Agent, or Firm*—Fish & Richardson P.C.

(57) ABSTRACT

The invention relates to a process for producing a flow cell for the spectroscopic analysis of samples to be passed through, the process comprising the following steps:

(a) provision of a first (10) and of a second (22) window, the second window (22) having at least two sample flow channels (24) for supplying and removing the sample to be analyzed;
(b) application of a structured thin layer (18) to one of the windows (10, 22);
(c) contacting and liquid-tight securing of the thin layer (18) to the other (22, 10) window, in such a way that facing, plane-parallel window surfaces (14, 20) of the windows (10, 22) and the thin layer (18) delimit a flow chamber (26) which is accessible only through the sample flow channels (24), the windows (10, 22) being optically transparent at least in some regions at least in the region of the flow chamber (26); and
(d) filling at least some regions of a filling chamber (28) between the windows (10, 22) which is separated from the flow chamber (26) by the thin layer (18) and adjoins the structured thin layer (18) with adhesive.

9 Claims, 2 Drawing Sheets

U.S. PATENT DOCUMENTS

| | | |
|---|---|---|
| 2004/0038387 A1 | 2/2004 | Howitz et al. |
| 2004/0092027 A1 | 5/2004 | Wolf et al. |

FOREIGN PATENT DOCUMENTS

| | | |
|---|---|---|
| DE | 195 24 795 | 1/1997 |
| DE | 197 38 626 | 3/1999 |
| DE | 197 39 126 | 4/1999 |
| DE | 199 09 692 | 3/2000 |
| DE | 101 04 957 | 3/2002 |
| GB | 2 261 285 | 5/1993 |
| WO | WO 02/21115 A1 * | 3/2002 |
| WO | WO02/057753 | 7/2002 |

* cited by examiner (a)

(b)

(c)

(d)

THIN-LAYER CELL

DESCRIPTION

The invention relates to a process for producing a flow cell according to claim 1.

Flow cells for the measurement of transmission are known and established in infrared spectroscopy. In such cells, the liquid sample to be analyzed is passed via sample feeding and removal channels through an optical measuring chamber which is delimited by infrared-transparent windows. The IR transmission spectrum measured may be evaluated, for example, by an FT-IR spectrometer (Fourier transformation infrared spectrometer). Depending on the application, different designs of such flow cells are used, which may be configured in a dismantleable and nondismantleable form.

The thicknesses of such cells, i.e. the distance between the cell windows which delimit the measuring chamber, in IR beam direction are generally between 0.015 mm and several millimeters. The dimensioning of the cell layer thickness depends substantially on the IR absorption behavior of the solvent used. Preference is given to using weakly absorbing solvents, for example carbon tetrachloride or carbon disulfide.

Water, in contrast, is a problematic solvent in infrared spectroscopy owing to its strong and wide-ranging absorption in the infrared spectral region. This is especially true in the middle infrared region of from 4000 to 400 $cm^{-1}$, since water has, for example at 1643 $cm^{-1}$, pronounced absorption behavior. Even at layer thicknesses of a few micrometers, this results in total absorption of the IR beam in the solvent in certain wavelength regions, so that these regions are analytically inaccessible. For many chemical, biochemical, pharmacological and physiologically interesting substances, water is, however, the natural solvent. The analysis of water-soluble substances is to an ever greater degree at the center of modern scientific and industrial studies and forms the focal point of many biological, medicinal and pharmaceutical investigations.

Owing to the IR absorption behavior of water, the cell layer thickness of flow cells for aqueous samples thus has to be kept small in order to obtain an evaluable transmission signal. The preferred layer thickness for transmission measurements of aqueous samples is, for example, stated to be from 6 to 7 µm by K. Rahmelow and W. Huber in Appl. Spectrosc. 51, 160-170 (1997). In "A stopped flow apparatus for infrared spectroscopy of aqueous solutions", Wharton et al. state that stopped-flow measurements which are usually used to investigate the kinetics of reactions cannot be carried out in transmission cells with the necessary layer thicknesses of approx. 5 µm (erroneously reported as 5 mm in the article). The cause of this is the enormously high flow resistance of such thin-layer measurement cells which is approximately inversely proportional to the layer thickness cubed, as a result of which high pressures arise at layer thicknesses of less than 10 µm.

Known dismantleable flow cells become leaky at relatively high pressures and the risk of cross-contamination of the samples becomes considerably higher. In addition, a uniform layer thickness after a pressurization or after dismantling is no longer ensured in the case of these cells. Natural limits are likewise placed on the layer thickness precision of dismantleable measuring cells by the given environmental conditions, for example dust. Dust particles in air are present mainly in a lower micrometer range, so that a high layer thickness precision can be achieved in the first assembly and in repeated assembly only under dust-free conditions. Reproducible measurements or quantitative determinations are therefore associated with high imprecision.

Known dismantleable flow cells are usually made of silver amalgam or lead amalgam and are designed only for a very low pressure of not more than 2 to 3 bar.

Owing to the above problems, alternative measurement systems for the IR characterization of aqueous samples have been proposed, for example in the form of ATR techniques (attenuated total reflection), in which the infrared beam, owing to physical laws, penetrates into the sample only by a few micrometers, but several times. However, a disadvantage of this technique is that the absorptions are wavelength-dependent and interface effects between optical material and the sample liquid, for example in the form of adsorption or denaturation of the sample (example: proteins), can occur.

In "Spectroscopy of Biological Molecules: New Directions; 8th European Conference on the Spectroscopy of Biological Molecules", Aug. 29-Sep. 2, 1999, Enschede, The Netherlands, edited by J. Greve, G. J. Puppels and C. Otto, pages 689 to 690, a flow cell was described whose production comprised a combination of photolithographic structuring techniques for the definition of a spacer between two IR-transparent windows with subsequent adhesion of the windows with an epoxy adhesive. Photolithographic structuring techniques are used in Microsystems technology preferably for the lateral structuring of photosensitive materials (coatings). They are less suitable for precise, uniform and reproducible material deposition in the form of a nonlaterally applied spacer layer. This is particularly true of layer thicknesses in the µm range. Here, this results in large layer thickness tolerances. Flow cells produced in this way have poorly reproducible flow and measurement chambers with dead zones and unsatisfactory plane-parallelism of the optical windows and insufficient layer thickness precision. Nowadays, IR spectrometers based virtually exclusively on the principle of Fourier transformation are used, which have distinct advantages over conventional spectrometers with regard to speed and measurement precision. There are correspondingly high demands on the optical sample chamber with regard to precise manufacture and the associated achievable measurement precision. In particular for the comparability and transferability of measurement results of strongly absorbing samples (for example aqueous solutions) of different measurement cells, a high precision and reproducibility of the layer thickness of the measurement cells and the plane-parallelism of the optical windows are of great significance (see Ramelow: "Fourier-Transformations-Infrarot-Spektroskopie—Von der Signalverarbeitung bis zur Sekundärstrukturbestimmung von Proteinen" [Fourier transformation infrared spectroscopy—from signal processing to secondary structure determination of proteins], HochschulVerlag, 1995). The transferability of measurement results to measurement systems of the same type is gaining ever greater importance with regard, for example, to utilization of spectral databases and the use of automated systems.

In view of the above disadvantages, it is an object of the invention to propose a process for producing high-precision and pressure-resistant flow cells which are suitable in particular for the precise and reproducible determination of strongly absorbing samples, for example of aqueous samples, by means of transmission IR spectroscopy.

The object is achieved by a process having the features specified in claim 1. Preferred embodiments are the subject matter of the dependent claims.

According to the invention, a process for producing a flow cell for the spectroscopic analysis of samples to be passed through comprises the following steps:

(a) provision of a first and of a second window, the second window having at least two sample flow channels for supplying and removing the sample to be analyzed;
(b) application of a structured thin layer to one of the windows;
(c) contacting and liquid-tight securing of the thin layer to the other window, in such a way that facing, plane-parallel window surfaces of the windows and the thin layer delimit a flow chamber which is accessible only through the sample flow channels, the windows being optically transparent at least in some regions at least in the region of the flow chamber; and
(d) filling at least some regions of a filling chamber between the windows which is separated from the flow chamber by the thin layer and adjoins the structured thin layer with adhesive.

The inventive flow cell is a nondismantleable thin-layer cell which is produced preferably by using micromechanical or planar-lithographic structuring techniques. The flow cell comprises two, preferably plate-shaped, windows with preferably planar window surfaces, each of which has at least one section transparent in the infrared spectral region. The liquid sample to be analyzed is passed through at least one sample flow channel of the second window (known as the flow head window) into a slot-like flow chamber between facing, plane-parallel window surfaces of the windows. A second sample flow channel allows the sample to be analyzed to be removed from the flow chamber. The flow chamber is optically accessible at least in some regions, so that the sample enclosed between the plane-parallel window surfaces of the two windows can be analyzed spectroscopically in transmission. In this context, for example, a Fourier spectrometer may be used.

The process according to the invention for producing the flow cell is notable in particular for the exact and reproducible geometric definition of the flow or sample chamber. To this end, a structured thin layer is applied on one of the windows and delimits the flow chamber along the slot between the plane-parallel window surfaces. The thin layer is preferably applied to one of the window surfaces with micromechanical or planar-lithographic structuring techniques. Subsequently, the other window is brought proximate to the first window, in such a way that the facing planar window surfaces run parallel to one another and the window surface of one window comes into contact with the structured thin layer. The bond between thin layer and window surface is accomplished by the thin layer being secured in a liquid-tight manner to the window surfaces of both windows. The structured thin layer thus forms a liquid-tight barrier layer which is bonded intimately to the window surfaces and delimits the flow chamber in the plane of the slot between the windows. The flow or sample chamber is thus accessible only through the sample flow channels.

The structured thin layer separates the flow chamber from a slot-like filling chamber which is likewise delimited by the plane-parallel window surfaces. For the permanent and exact fixing of the positional alignment of the two windows relative to one another, the filling chamber is filled at least in some regions with adhesive. The adhesive wets the facing window surfaces of the filling chamber and preferably also the structured thin layer delimiting the slot region. After the adhesive has set, a pressure-resistant and reproducible flow cell is provided and is suitable in an outstanding manner for the infrared spectroscopy analysis of aqueous samples. The liquid-tight securing of the thin layer to both window surfaces results in no gap existing between the window surfaces and the thin layer, through which adhesive might penetrate into the flow chamber or into the gap in the subsequent filling step.

The function of the sealed flow chamber serves in particular for defined adhesive flow in step (d), so that penetration of the adhesive as a result of capillary forces or under pressure into the flow chamber is prevented. When there is no leak-proof bond between the structured thin layer and the second window, penetration of the adhesive into the (nano)gap between structured thin layer and flow head as a result of capillary force cannot be ruled out. This results in an insufficiently defined adhesive interface layer. If the thin layer is to be removed after the adhesive has set, the result in this case would be unsatisfactory flow geometry. In contrast, the process according to the invention enables the formation of smooth interface surfaces of the flow chamber without dead zones.

The predefined structure of the adhesive surface (indirect structuring of the adhesive) results advantageously in no demands being made on the adhesive with regard to microstructuring capability. This allows a multitude of adhesives to be used which are optimized according to the demands such as solvent resistance, elasticity or adhesion in particular applications, for example the use of aggressive solvents, high pressure and thermal resistance. Typical adhesives for this application are single-component or multicomponent systems, for example polyamides, polyester urethanes, epoxides, polyacrylates (PMMA), cyanoacrylates, silicones and polyimides. The curing system of the adhesive can be induced to react by light (e.g. UV and/or VIS), heat, atmospheric moisture, or anaerobically by means of metal contact and/or with activator. The activator (applied to one or both sides of the window) may initiate the curing by a free-radical, anionic or cationic mechanism. Combinations are also possible, for example UV+anaerobic curing; this allows, for example, regions to be reached which are not accessible with light and cure by virtue of the secondary system. Adhesives may be elasticized, for example, by addition of long-chain alcohols in order to better compensate stresses in the event of pressurizations. Adhesives may be electrically conductive, in order, for example, to serve as an electrode for electrochemical measurements.

For the production of the windows, preference is given to using IR-transparent materials, for example calcium fluoride, barium fluoride, zinc selenide, zinc sulfide, silicon, germanium, potassium bromide, sodium chloride and/or silver halide. It is also possible to optimize various materials using polymer coatings for corresponding application requirements, for example water insolubility or biocompatibility. Possible polymers are, for example, Parylene, PTFE and PE.

With the aid of the microstructuring of the thin layer, it is possible to realize any flow geometries which are tailored for particular objectives and ensure a very small, dead zone-free, optical flow and measurement chamber. For example, it is possible to realize flow chambers having a volume of less than 10 nl. This results in a small sample requirement and a lower risk of cross-contamination with the preceding or following sample. In addition, the flushing times and volumes between two measurements can be distinctly reduced. With regard to automated high-throughput use, for example for pharmaceutical screening or in the analysis of expensive samples, for example proteins which are difficult to express, flow cells produced by the process according to the invention thus have considerable advantages over conventional flow cells.

It is possible by the process to produce measurement cells as nondismantleable units which ensure a high pressure resistance and a high resistance toward stresses arising from pressure change in the range from 0 (external vacuum) to 400 bar with extremely short pressure relaxation times. The pressure relaxation time refers to the time which the measurement cell requires in the transition from the pressure-stressed to the unstressed state to recover its original layer thickness. In this context, the demands on precise measurement cells are at a layer thickness constancy between reference and subsequent sample measurement of less than 1 nm (see Ramelow: "Fourier-Transformations-Infrarot-Spektroskopie—Von der Signalverarbeitung bis zur Sekundärstrukturbestimmung von Proteinen", HochschulVerlag, 1995), so that no errors which can be measured by IR spectroscopy can be detected. For kinetic measurements or for automated high-throughput use for instance, the aim is to attain this state as rapidly as possible (rapid pressure relaxation). Flow measurement cells produced by the process according to the invention are within the lower millisecond range. In contrast, conventional dismantleable measurement cells have a distinctly slower pressure relaxation of a few seconds up to minutes, and a deviation from the original layer thickness (layer thickness before the pressurization) which can be measured by IR spectroscopy generally remains. In addition, the measurement cells produced by the process according to the invention are guaranteed to be leakproof even at relatively high temperatures, for example when measuring temperature ramps. Conventional dismantleable measurement cells are sufficiently leakproof only up to approx. 60° C. Depending on the selection of the adhesive, the inventive measurement cells may be used from −60° C. to +230° C., preferably from +4 to +90° C.

The manufacture of the measurement cells described here by microsystems technology proceeds preferably under cleanroom conditions and ensures a virtually dust-free environment in the manufacture, which can achieve a particularly high layer thickness precision.

In a preferred embodiment of the process according to the invention, the liquid-tight securing of the thin layer to the other window includes a softening of the thin layer to temporarily lower its viscosity by increasing the temperature of the thin layer and/or by increasing the pressure applied on the thin layer to the other window. Preference is given to achieving the intimate, liquid-tight bond of the thin layer with the window surface by incipiently or fully melting the thin layer. The softening of the thin layer lowers its viscosity in such a way that the window surface of the proximate window is wetted fully by the softened thin layer in order to form an intimate, liquid-tight bond after cooling. In the selection of suitable thin layer materials, a lowering in viscosity may also be brought about by an increase in the pressure applied by the thin layer to the other window. The intimate, liquid-tight bond of the thin layer to the two window surfaces enables a precise and reproducible definition of the flow chamber and a liquid-tight partition of this chamber from the filling chamber.

The thin layer should preferably consist of a material which, with regard to the configuration of the flow chamber, enables various structures or microstructures and at the same time permits liquid-tight sealing between the first window (spacer window) and the second window (flow head window). It should preferably be possible to remove the material again by means of a suitable solvent. Conceivable examples of materials are photoresists, lacquers and polymers. For the application and structuring of the thin layer, preference is given to using processes such as photolithography or screenprinting.

In a further embodiment of the invention, the thin layer consists of a viscous material having a viscosity of at least 10 000 mPas at a temperature of 20° C. and the liquid-tight securing of the thin layer to the other window includes the step of pressing the viscous thin layer onto the other window.

In this embodiment of the process according to the invention, the structured thin layer consists of a comparatively highly viscous material which, when contacted with or pressed onto the window surface to be brought proximate, wets it in such a way that a liquid-tight and gapless bond is formed between thin layer and window. Thus, no adhesive can pass from the filling chamber into the flow chamber through any gap in a subsequent filling step. Alternatively, a low-viscosity material may also be used which, after the gapless bonding between thin layer and window, can be brought into a highly viscous and dimensionally stable state by a further treatment, for example heating (e.g. viscosity increase as a result of solvent evaporation from the material) or illumination. In this context, particular preference, is given to using light-curing adhesives which are brought from a low-viscosity to a high-viscosity state by the action of light. The adhesives may be applied, for example, by a screen-printing process.

In a particularly preferred embodiment of the invention, a structured spacer layer with predetermined layer thickness is applied to one of the window surfaces of at least one of the windows, and the spacer layer comes into contact with the window surface of the other window in step (c) in such a way that the distance between the window surfaces is determined by the thickness of the spacer layer. In this inventive embodiment, a separate spacer layer is applied to one of the window surfaces in addition to the structured thin layer which is responsible essentially for the geometric definition of the flow chamber. The main function of the spacer layer is to ensure a reproducible, predetermined and plane-parallel separation between the surfaces of the windows.

For the application of the spacer layer, preference is given to using methods such as sputtering, vapor deposition, ion plating, PVD, CVD, PECVD, wet-chemical metal deposition and/or laser-supported material deposition, which ensure a high precision and reproducibility with regard to the material deposition. Also suitable to a limited extent are screenprinting techniques and photolithographic processes. Particularly advantageous methods are those in which the material thickness applied can be controlled exactly, so that predetermined spacer layer thicknesses can be achieved reproducibly. The spacer layer is preferably not deformable thermally or under pressure. In this way, it is possible to adjust the slot thickness of the optical flow chamber reproducibly and precisely.

It is possible with the abovementioned preferred production techniques to precisely and reproducibly establish layer thicknesses over a preferred range of from 0.5 to 100 μm, more preferably from 1 to 50 μm and most preferably from 3 to 15 μm. The resulting, likewise high parallelism of the optical windows relative to one another (same layer thickness at each point within the flow cell) enables very precise quantitative analysis of the sample, since disruptive optical effects, for example light scattering, reflection or beam inhomogeneity in the course of beam passage are minimized. The flow cells produced by the process according to the invention thus enable precise calibration and high reproducibility and comparability of measurements which have been taken in different flow cells. The transferability of measurements of identical measurement systems in particular is playing an ever greater role in spectroscopic application, for example spectral databases.

A further significant advantage of the inventive flow cells is the guarantee of uniform liquid flow within the slot-like flow chamber, so that the windows should preferably have high parallelism relative to one another. A wedge arrangement of the windows may lead, in the region of the smallest slot thickness of the, slot-like flow chamber, to zones of poor flow (known as dead zones). The spacer layer ensures reproducibly that the planar window surfaces can be aligned plane-parallel relative to one another without the complicated window positioning devices being necessary.

Preference is given to applying the spacer layer in an edge region of the window. Such an arrangement of the spacer layer ensures in a particularly efficient manner high plane-parallelism of the window surfaces which are spaced apart. At the same time, the spacer layer is positioned comparatively far from the flow chamber which is preferably formed in the central region of the window surfaces, so that a comparatively large filling chamber is formed. This enables adhesion of the windows over a large surface area by filling of the filling chamber.

The thin layer preferably has a complete circular shape. In this case, the circular shape of the thin layer is positioned with respect to the sample flow channels in such a way that they are preferably very close to the thin layer in order to minimize disadvantageous dead zones. With the aid of structuring processes from microsystems technology, it is also possible to construct complex flow geometries which are adapted to the particular requirements, for example the integration of electrodes.

At least one of the windows preferably has at least one adhesive channel for feeding the adhesive into the filling chamber. Particular preference is given to an embodiment with two adhesive channels in which the second adhesive channel serves as an adhesive outlet orifice. Particular preference is likewise given to an embodiment with two adhesive channels in which both channels serve as adhesive inlets and the spacer layer is interrupted at suitable points, these points serving as adhesive outlets. The adhesive is either injected into the filling chamber by pressure application or introduced via the capillary effect.

Preference is given to removing the thin layer after step (d). In the case of thin layers which are solvent-soluble, this may be effected, for example, by flushing the flow chamber with a solvent. The separation of the window surfaces after step (d) is preferably in the range from 0.5 to 100 μm, preferably from 1 to 15 μm and most preferably from 3 to 15 μm.

DESCRIPTION OF THE DRAWINGS

The invention is described by way of example hereinbelow with reference to accompanying drawings of a preferred working example. The figures show.

DETAILED DESCRIPTION OF THE INVENTION

Figure 1:
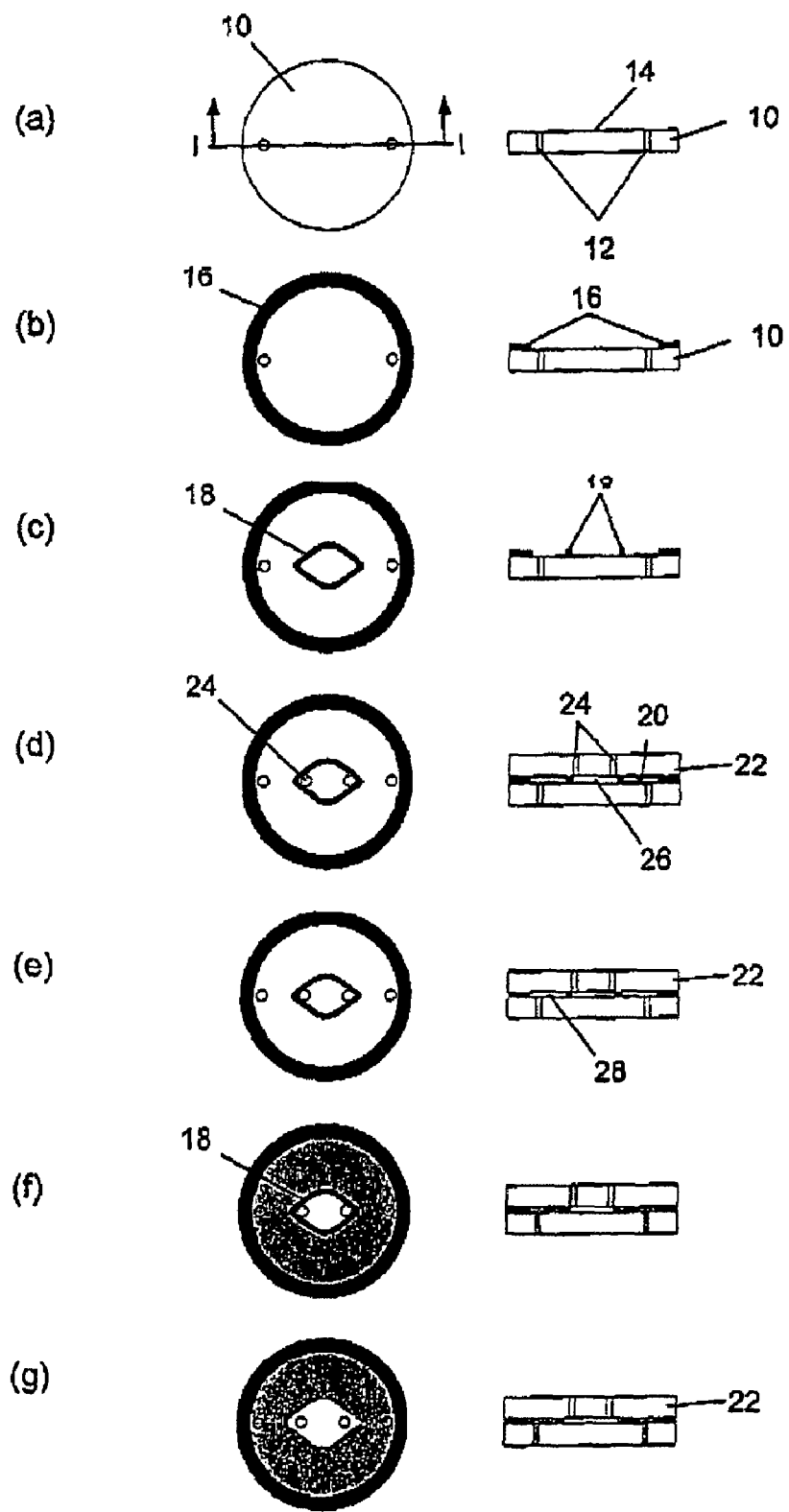
FIG. 1 production stages of a flow cell during a preferred variant of the production process according to the invention in schematic view (left-hand column) and schematic cross section (right-hand column)

FIG. 1 (*a*) to (*g*) each show, in schematic plan views and cross-sectional views along the line I-I, essential process stages of a preferred variant of the process according to the invention for producing flow cells. As shown in FIG. 1(*a*), an IR-transparent window 10 is used in this preferred process and has two adhesive channels 12. A circular spacer layer 16 is defined preferably by micromechanical or planar-lithographic structuring techniques on a planar window surface 14 of the window 10, said circular spacer layer 16 preferably consisting of a material which is substantially incompressible and very substantially not thermally deformable (for example a metal) (FIG. 1(*b*)). The layer thickness of the spacer layer 16 is controlled in such a way that it corresponds to the desired later slot separation between the two plane-parallel windows.

Subsequently, as shown in FIG. 1(*c*), a structured thin layer 18 is applied to the window surface 14 of the window 10. The thin layer 18 has a circular shape and serves to geometrically define the flow chamber. The layer thickness of the thin layer 18 is not less than that of the spacer layer 16, so that it can come into contact with a window surface 20 of a second window 22 when it is moved proximate to the window 10. In the window 22, which is also referred to as the flow head window, two sample flow channels 24 are formed, through which the liquid sample can be admitted to and discharged from a flow chamber 26. The flow chamber 26 is delimited laterally (i.e. in the plane of the slot) by the circular thin layer 18 and connected to the environment only through the sample flow channels 24. The circular thin layer 18 separates the flow chamber 26 from a filling chamber 28 which adjoins the thin layer 18 (FIG. 1(*d*)).

After the window surface 20 has been contacted to the thin layer 18 and the spacer layer 16, an intimate, liquid-tight adhesive bond to the window surface 20 is generated preferably by a softening or adhesion or reshaping process of the thin layer, so that no gap remains between the thin layer 18 and the window surface 20. Equally, no gap must remain between the thin layer 18 and the window surface 14 of the window 10 either. In this state shown in FIG. 1(*e*), the filling chamber 28 is separated hermetically and gaplessly from the flow chamber 26.

In this state, as shown in FIG. 1(*f*), an adhesive is injected through one of the adhesive channels 12 into the filling chamber 28 until it is filled fully with adhesive. In the course of this filling, the adhesive fully adjoins the circular thin layer 18. In an optional subsequent step, as shown in FIG. 1(*g*), the thin layer 18 can be removed, so that the flow chamber 26 is now delimited by the adhesive layer in the plane of the slot. In FIG. 1, the adhesive is emphasized by gray shading.

Figure 2:
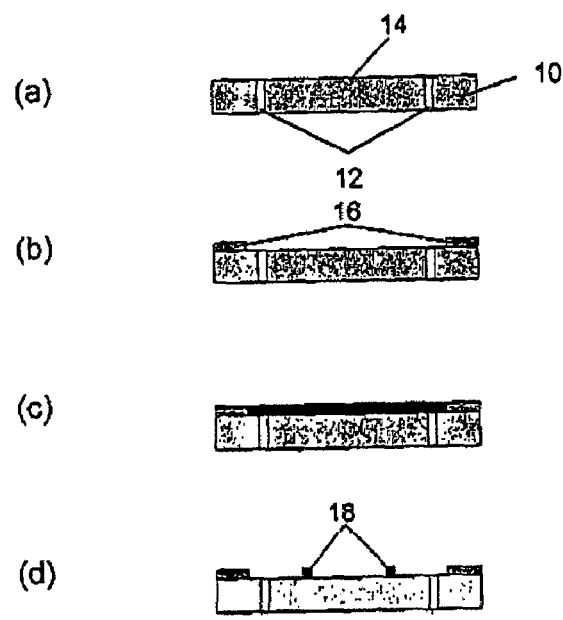
FIG. 2 schematic cross-sectional views of different production stages of a flow cell during one variant of the production process according to the invention.

In FIG. 2, the sequence of steps shown in FIG. 1(*a*) to (*c*) in a particularly preferred embodiment is shown once again in detail. The spacer layer 16 is initially applied with a defined layer thickness to the window 10, shown in FIG. 2(*a*), for example by means of screenprinting technology or a vapor deposition or sputtering technique and lithographic structuring. Subsequently, the window surface 14 is coated with a photoresist layer with defined layer thickness by means of a spincoater. In this context, the resist layer thickness is slightly greater than that of the spacer layer 16. FIG. 2(*d*) shows the finished structured thin layer 18 after completion of the subsequent lithography and removal step.

Figure 3:
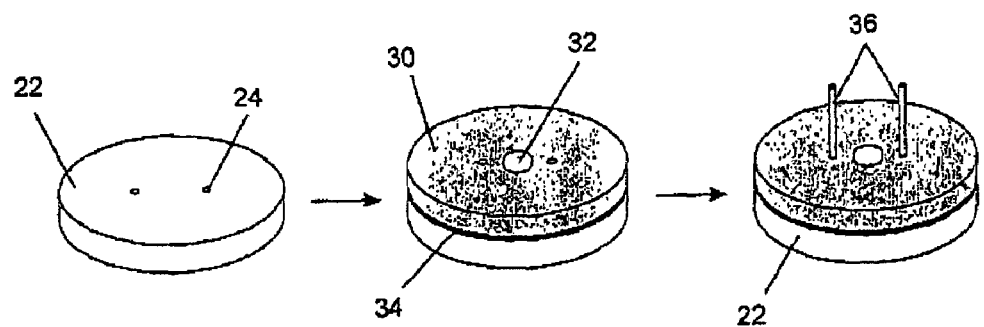
FIG. 3 schematic perspective view of a measurement cell apparatus comprising an inventive flow cell.

The finished measurement cell apparatus (the flow head) is constructed preferably in the form shown in FIG. 3. A metal plate 30 with at least two drillholes for the sample flow channels 12 and with at least one cutout 32 for the optical beam path is preferably bonded to the window 22 in such a way that the drillholes of the metal plate 30 are preferably bonded to one another with precise fitting or via channels in the window 22 or in the metal plate 30 or a sealant material 34. The sealing between the window 22 and the metal plate 30 may be effected by adhesive bonding or by sealants 34. The connections to the inlets and the outlets may be such that precisely fitting capillaries 36 are conducted through the drill holes of the metal plate 30, of the sealant material 34 and of the window 22, and are ended by HPLC connections which are present in the metal plate 30 or are pressure-tight and substantially dead zone-free by virtue of adhesive bonding.

The capillaries 36 preferably end planar to the window underside 20, i.e. end directly before the thin layer.

REFERENCE NUMERAL LIST

10 window (spacer window)
12 adhesive channels
14 window surface of the window 10
16 spacer layer
18 structured thin layer
20 window surface of the window 22
22 window (flow head window)
24 sample flow channels
26 flow or sample chamber
28 filling chamber
30 metal plate
32 cutout
34 sealant material
36 capillaries

What is claimed is:

1. A process for producing a flow cell for the spectroscopic analysis of samples to be passed through, the process comprising the following steps:
   (a) provision of a first and of a second window, the second window having at least two sample flow channels for supplying and removing the sample to be analyzed;
   (b) application of a structured thin layer to one of the windows;
   (c) contacting and liquid-tight securing of the thin layer to the other window, in such a way that facing, plane-parallel window surfaces of the windows and the thin layer delimit a flow chamber which is accessible only through the sample flow channels, the windows being optically transparent at least in some regions at least in the region of the flow chamber; and
   (d) filling at least some regions of a filling chamber between the windows which is separated from the flow chamber by the thin layer and adjoins the structured thin layer with adhesive, and the liquid-tight securing of the thin layer to the other window includes a softening of the thin layer to temporarily lower its viscosity by increasing the temperature of the thin layer and/or by increasing the pressure applied on the thin layer to the other window, and wherein the thin layer is removed after step (d).

2. The process as claimed in claim 1, wherein the thin layer consists of a viscous material having a viscosity of at least 10000 mPas at a temperature of 20° C. and the liquid-tight securing of the thin layer to the other window includes the step of pressing the viscous thin layer onto the other window.

3. The process as claimed in claim 1, wherein a structured spacer layer with predetermined layer thickness is applied to one of the window surfaces of at least one of the windows, and the spacer layer comes into contact with the window surface of the other window in step (c) in such a way that the distance between the window surfaces is determined by the thickness of the spacer layer.

4. The process as claimed in claim 3, wherein the spacer layer is applied in an edge region of the window.

5. The process as claimed in claim 1, wherein the thin layer has a complete circular shape.

6. The process as claimed in claim 1, wherein at least one of the windows has at least one adhesive channel for feeding the adhesive into the filling chamber.

7. The process as claimed in claim 1, wherein the distance between the window surfaces after step (d) is in the range from 0.5 to 100 μm.

8. The process as claimed in claim 1, wherein the distance between the window surface after step (d) is in the range from 1 to 50 μm.

9. The process as claimed in claim 1, wherein the distance between the window surface after step (d) is in the range from 3 to 15 μm.

* * * * *

UNITED STATES PATENT AND TRADEMARK OFFICE
CERTIFICATE OF CORRECTION

PATENT NO. : 7,479,197 B2  Page 1 of 1
APPLICATION NO. : 10/530956
DATED : January 20, 2009
INVENTOR(S) : Ralf Masuch It is certified that error appears in the above-identified patent and that said Letters Patent is hereby corrected as shown below:

Column 10; line 34:
In Claim 9, delete "surface" and insert -- surfaces --, therefor.

Signed and Sealed this

Thirty-first Day of March, 2009

JOHN DOLL
*Acting Director of the United States Patent and Trademark Office*